United States Patent [19]

Costin et al.

[11] Patent Number: 4,804,671

[45] Date of Patent: Feb. 14, 1989

[54] 1-(TRIHALOMETHYLSULFENYL)-4-ARYL-1,2,4-TRIAZOLIN-5-ONES AND FUNGICIDES CONTAINING THESE COMPOUNDS

[75] Inventors: Rentzea Costin, Heidelberg; Sabine Thym, Dossenheim; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 941,528

[22] Filed: Dec. 18, 1986

Related U.S. Application Data

[63] Continuation of Ser. No. 674,484, Nov. 26, 1984, abandoned, which is a continuation of Ser. No. 409,669, Aug. 19, 1982, abandoned.

[30] Foreign Application Priority Data

Aug. 24, 1981 [DE]  Fed. Rep. of Germany ....... 3133405

[51] Int. Cl.$^4$ ..................... A01N 43/64; A01N 47/04; C07D 249/12
[52] U.S. Cl. .................................. 514/384; 548/264; 548/265
[58] Field of Search ........................ 548/264; 514/384

[56] References Cited

U.S. PATENT DOCUMENTS

| | | | |
|---|---|---|---|
| 4,088,767 | 5/1978 | Shigematsu et al. | 548/264 |
| 4,098,896 | 7/1978 | Edwards | 514/384 |
| 4,120,864 | 10/1978 | Seipez et al. | 548/264 |
| 4,350,701 | 9/1982 | Rentzea et al. | 548/263 |

OTHER PUBLICATIONS

Chemical Week, Jun. 21, 1972, p. 63.

Primary Examiner—Richard L. Raymond
Assistant Examiner—Patricia L. Morris
Attorney, Agent, or Firm—Keil & Weinkauf

[57] ABSTRACT 1-(trihalomethylsulfenyl)-4-aryl-1,2,4-triazolidin-5-ones of the formula

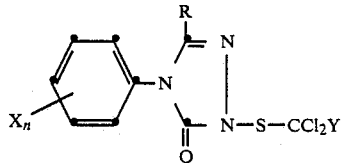

where R is substituted or unsubstituted alkyl, or is alkenyl or cycloalkyl, X is hydrogen, halogen, substituted or unsubstituted alkyl or alkoxy, alkenyl, cyano, nitro, or substituted or unsubstituted phenyl or phenoxy, n is an integer from 1 to 5, and Y is fluorine or chlorine, and fungicides containing these compounds.

3 Claims, No Drawings

1-(TRIHALOMETHYLSULFENYL)-4-ARYL-1,2,4-TRIAZOLIN-5-ONES AND FUNGICIDES CONTAINING THESE COMPOUNDS

This application is a continuation of application Ser. No. 674,484, filed Nov. 26, 1984, abandoned, which is a continuation of application Ser. No. 409,669, filed Aug. 19, 1982, abandoned.

The present invention relates to novel, useful 1-(trihalomethyl-sulfenyl)-4-aryl-1,2,4-triazolidin-5-ones having a fungicidal action, their use for controlling phytopathogenic fungi, and fungicides containing these compounds.

Chemical Week, 21st June, 1972, page 63 discloses that N-trichloromethylthio-tetrahydrophthalimide can be used for controlling phytopathogenic fungi. However, its action on other Phycomycetes, eg. *Phytophthora infestans* in tomatoes or potatoes, is unsatisfactory, and its action is also inadequate for protecting materials or protecting wood against discoloring fungi.

U.S. Pat. No. 4,098,896 furthermore discloses that 4-substituted 1-halohydrocarbylthio-3-hydrocarbylthio-1,2,4-triazolidin-5-ones can be used as fungicides. The compound 1-trichloromethylthio-3-methylthio-4-p-methoxy-m-chlorophenyl-1,2,4-triazolidin-5-one falls within the scope of this publication.

We have found that the novel 1-(trihalomethylsulfenyl)-4-aryl-1,2,4-triazolidin-5-ones of the general formula

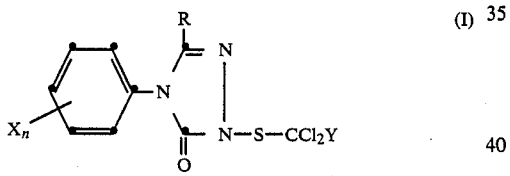

(I)

where R is alkyl of 1 to 6 carbon atoms which is unsubstituted or substituted by methoxy or ethoxy, or is alkenyl of 2 to 6 carbon atoms, or is cycloalkyl of 3 to 7 carbon atoms which is unsubstituted or substituted by methoxy, X is hydrogen, halogen (eg. fluorine, chlorine, bromine or iodine), alkyl or alkoxy of 1 to 5 carbon atoms which is unsubstituted or substituted by fluorine, chlorine or bromine, or alkenyl of 2 to 4 carbon atoms, cyano or nitro, or is phenyl or phenoxy which may be substituted by fluorine, chlorine, bromine or alkyl of 1 to 4 carbon atoms, n is an integer from 1 to 5 and Y is fluorine or chlorine, have a powerful fungicidal action. The novel substances have a good action spectrum and can be used, in particular, on Phycomycetes and *Fungi imperfecti*, and also on Ascomycetes and Basidiomycetes. They are suitable, for example, for use in crop protection for controlling phytopathogenic fungi, and do not damage the crops when used in the required concentrations. They are also outstandingly suitable for protecting materials and for protecting wood against species of fungi such as Sclerophoma and Pullullaria.

We have also found that the compounds of the general formula (I) are obtained by a process wherein a 4-aryl-1,2,4-triazolidin-5-one of the formula (II)

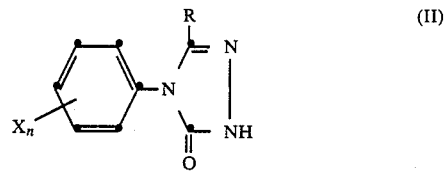

where R, X, Y and n have the above meanings, is reacted with a sulfenyl chloride of the formula YCCl₂—S—Cl (III), where Y has the above meanings, in the presence or absence of an acid acceptor and in the presence or absence of a solvent or diluent, advantageously as a one-phase or two-phase reaction in a solvent or diluent which is inert towards the reactants, for example water, toluene, xylene, diethyl ether, tetrahydrofuran, dioxane, dimethoxyethane, acetone, methyl ethyl ketone, ethyl acetate, methylene chloride, chloroform, dichloromethane or chlorobenzene.

Examples of acid acceptors include inorganic bases, such as hydroxides and carbonates of alkali metals and alkaline earth metals, eg. NaOH, NaHCO₃, KHCO₃, K₂CO₃, CaCO₃ and BaCO₃, and, in particular, tertiary amines, such as triethylamine, N,N-dimethylcyclohexylamine, N,N-dimethylaniline and pyridine.

The reactions are carried out at, for example, from $-30°$ to $+100°$ C., preferably from $-10°$ to $+25°$ C., under atmospheric pressure.

The novel compounds of the general formula (I) where Y is fluorine are also obtained by a process wherein a 1,2,4-triazolidin-5-one of the formula Ia

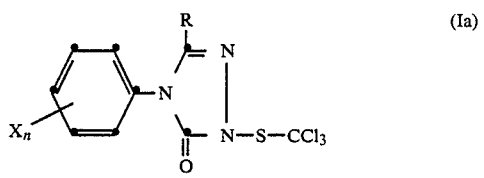

(Ia)

where R, X and n have the above meanings, is reacted with anhydrous hydrofluoric acid, in order to replace one chlorine atom in the trichloromethylthio side chain by fluorine. The reaction with a compound of the formula Ia can be carried out in excess hydrofluoric acid, as the diluent, at from $-50°$ to $+80°$ C., preferably $-10°$ to $+25°$ C., under atmospheric or superatmospheric pressure.

X is preferably hydrogen, fluorine, chlorine, bromine, methyl, ethyl, isopropyl, tert.-butyl, trifluoromethyl, nitro, methoxy, ethoxy, tetrafluoroethoxy, phenoxy or phenyl, and n is preferably 1, 2, 3 or 4.

R is preferably methyl, ethyl, n-propyl, isopropyl, n-butyl, isobutyl, sec.-butyl, tert.-butyl, n-pentyl, isopentyl, methoxymethyl, 2-methoxyethyl, 2-ethoxyethyl, cyclopropyl, cyclopentyl, cyclohexyl or 4-methoxycyclohexyl.

Formula (II) provides a general definition of the 4-aryl-1,2,4-triazolidin-5-ones used as starting materials.

The starting msterials of the formula (II) are known (cf. H. Gehlen and W. Schade, Liebigs Ann. Chem., 675 (1964), 180 and M. Pesson and S. Dupin, Bull. Soc. Chim. Fr., 250 (1962)). Those which are not known can be obtained in a conventional manner by cyclizing a 1-aryl-4-formyl-semicarbazide in the presence of an alkali metal hydroxide.

The starting materials of the formula (II) which have been used for the preparation of the novel compounds of the formula (I) are described in detail in Table 1.

The formula (Ia) provides a general definition of the 1-trichloromethyl-sulfenyl-4-aryl-1,2,4-triazolidin-3-ones also required for the preparation of the novel substances. They can be prepared by processes which are known in principle and are customary in the laboratory. Relevant data can be found in the preparation examples.

Finally, the trihalomethyl-sulfenyl chlorides of the formula III required for the preparation of the novel substances are generally known.

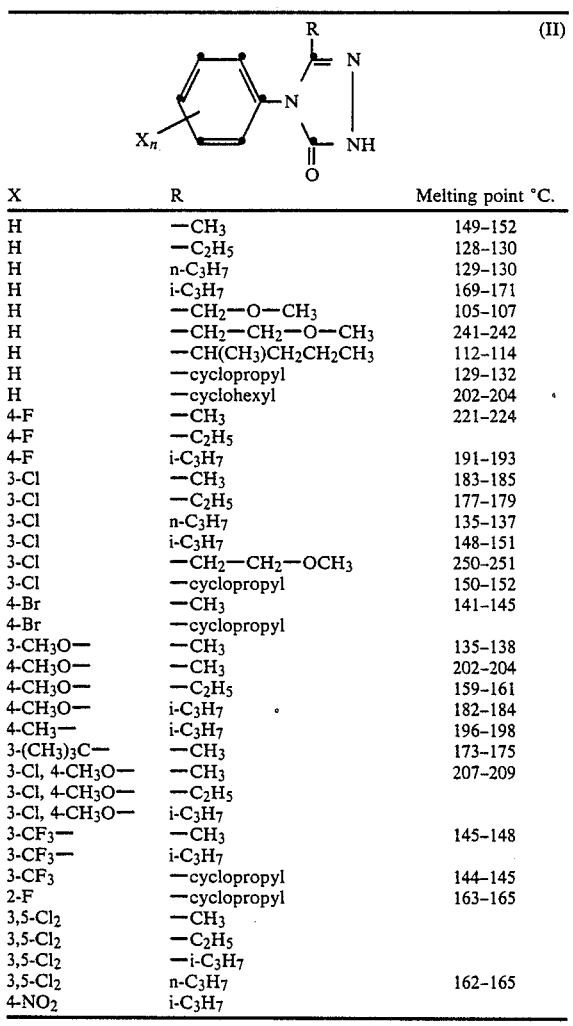

| X | R | Melting point °C. |
|---|---|---|
| H | —CH₃ | 149–152 |
| H | —C₂H₅ | 128–130 |
| H | n-C₃H₇ | 129–130 |
| H | i-C₃H₇ | 169–171 |
| H | —CH₂—O—CH₃ | 105–107 |
| H | —CH₂—CH₂—O—CH₃ | 241–242 |
| H | —CH(CH₃)CH₂CH₂CH₃ | 112–114 |
| H | —cyclopropyl | 129–132 |
| H | —cyclohexyl | 202–204 |
| 4-F | —CH₃ | 221–224 |
| 4-F | —C₂H₅ | |
| 4-F | i-C₃H₇ | 191–193 |
| 3-Cl | —CH₃ | 183–185 |
| 3-Cl | —C₂H₅ | 177–179 |
| 3-Cl | n-C₃H₇ | 135–137 |
| 3-Cl | i-C₃H₇ | 148–151 |
| 3-Cl | —CH₂—CH₂—OCH₃ | 250–251 |
| 3-Cl | —cyclopropyl | 150–152 |
| 4-Br | —CH₃ | 141–145 |
| 4-Br | —cyclopropyl | |
| 3-CH₃O— | —CH₃ | 135–138 |
| 4-CH₃O— | —CH₃ | 202–204 |
| 4-CH₃O— | —C₂H₅ | 159–161 |
| 4-CH₃O— | i-C₃H₇ | 182–184 |
| 4-CH₃— | i-C₃H₇ | 196–198 |
| 3-(CH₃)₃C— | —CH₃ | 173–175 |
| 3-Cl, 4-CH₃O— | —CH₃ | 207–209 |
| 3-Cl, 4-CH₃O— | —C₂H₅ | |
| 3-Cl, 4-CH₃O— | i-C₃H₇ | |
| 3-CF₃— | —CH₃ | 145–148 |
| 3-CF₃— | i-C₃H₇ | |
| 3-CF₃ | —cyclopropyl | 144–145 |
| 2-F | —cyclopropyl | 163–165 |
| 3,5-Cl₂ | —CH₃ | |
| 3,5-Cl₂ | —C₂H₅ | |
| 3,5-Cl₂ | —i-C₃H₇ | |
| 3,5-Cl₂ | n-C₃H₇ | 162–165 |
| 4-NO₂ | i-C₃H₇ | |

Specific examples of the novel active ingredients of the formula I are 1-trichloromethyl-sulfenyl-3-methyl-4-phenyl-1,2,4-triazolidin-5-one, 1-fluorodichloromethylsulfenyl-3-methyl-4-phenyl-1,2,4-triazolidin-5-one, 1-trichloromethyl-sulfenyl-3-ethyl-4-phenyl-1,2,4-triazolidin-5-one, 1-trichloromethyl-sulfenyl-3-propyl-4-phenyl-1,2,4-triazolidin-5-one, 1-trichloromethyl-sulfenyl-3-isopropyl-4-phenyl-1,2,4-triazolidin-5-one, 1-fluorodichloromethyl-sulfenyl-3-isopropyl-4-phenyl-1,2,4-triazolidin-5-one, 1-trichloromethyl-sulfenyl-3-methoxymethyl-4-phenyl-1,2,4-triazolidin-5-one, 1-trichloromethyl-sulfenyl-3-(2-methoxyethyl)-4-phenyl-1,2,4-triazolidin-5-one, 1-fluorodichloromethyl-sulfenyl-3-(2-methoxyethyl)-4-phenyl-1,2,4-triazolidin-5-one, 1-trichloromethyl-sulfenyl-3-cyclopropyl-4-phenyl-1,2,4-triazolidin-5-one, 1-fluorodichloromethyl-sulfenyl-3-cyclopropyl-4-phenyl-1,2,4-triazolidin-5-one, 1-trichloromethyl-sulfenyl-3-(pent-2-yl)-4-phenyl-1,2,4-triazolidin-5-one, 1-fluorodichloromethyl-sulfenyl-3-(pent-2-yl)-4-phenyl-1,2,4-triazolidin-5-one, 1-trichloromethyl-sulfenyl-3-cyclohexyl-4-phenyl-1,2,4-triazolidin-5-one, 1-fluorodichloromethyl-sulfenyl-3-cyclohexyl-4-phenyl-1,2,4-triazolidin-5-one, 1-trichloromethyl-sulfenyl-3-methyl-4-(4-fluorophenyl)-1,2,4-triazolidin-5-one, 1-trichloromethyl-sulfenyl-3-ethyl-4-(4-fluorophenyl)-1,2,4-triazolidin-5-one, 1-fluorodichloromethyl-sulfenyl-3-methyl-4-(4-fluorophenyl)-1,2,4-triazolidin-5-one, 1-fluorodichlormethyl-sulfenyl-3-ethyl-4-(4-fluorophenyl)-1,2,4-triazolidin-5-one, 1-trichloromethyl-sulfenyl-3-isopropyl-4-(4-fluorophenyl)-1,2,4-triazolidin-5-one, 1-trichloromethyl-sulfenyl-3-methoxymethyl-4-(4-fluorophenyl)-1,2,4-triazolidin-5-one, 1-fluorodichloromethyl-sulfenyl-3-isopropyl-4-(4-fluorophenyl)-1,2,4-triazolidin-5-one, 1-fluorodichloromethyl-sulfenyl-3-methoxymethyl-4-(4-fluorophenyl)-1,2,4-triazolidin-5-one, 1-trichloromethyl-sulfenyl-3-cyclopropyl-4-(4-fluorophenyl)-1,2,4-triazolidin-5-one, 1-fluorodichloromethyl-sulfenyl-3-cyclopropyl-4-(4-fluorophenyl)-1,2,4-triazolidin-5-one, 1-trichloromethyl-sulfenyl-3-cyclohexyl-4-(4-fluorophenyl)-1,2,4-triazolidin-5-one, 1-fluorodichloromethyl-sulfenyl-3-cyclohexyl-4-(4-fluorophenyl)-1,2,4-triazolidin-5-one, 1-trichloromethyl-sulfenyl-3-(2-methoxyethyl)-4-(4-fluorophenyl)-1,2,4-triazolidin-5-one, 1-fluorodichloromethylsulfenyl-3-cyclopropyl-4-(4-fluorophenyl)-1,2,4-triazolidin-5-one, 1-trichloromethyl-sulfenyl-3-methyl-4-(4-chlorophenyl)-1,2,4-triazolidin-5-one, 1-trichloromehyl-sulfenyl-3-ethyl-4-(4-chlorophenyl)-1,2,4-triazolidin-5-one, 1-fluorodichloromethyl-sulfenyl-3-methyl-4-(4-chlorophenyl)-1,2,4-triazolidin-5-one, 1-fluorodichloromethyl-sulfenyl-3-ethyl-4-(4-chlorophenyl)-1,2,4-triazolidin-5-one, 1-trichloromethyl-sulfenyl-3-isopropyl-4-(4-chlorophenyl)-1,2,4-triazolidin-5-one, 1-fluorodichloromethyl-sulfenyl-3-isopropyl-4-(4-chlorophenyl)-1,2,4-triazolidin-5-one, 1-trichloromethyl-sulfenyl-3-methyl-4-(3-chlorophenyl)-1,2,4-triazolidin-5-one, 1-fluorodichloromethyl-sulfenyl-3-methyl-4-(4-chlorophenyl)-1,2,4-triazolidin-5-one, 1-fluorodichloromethyl-sulfenyl-3-methyl-4-(3-chlorophenyl)-1,2,4-triazolidin-5-one, 1-trichloromethyl-sulfenyl-3-ethyl-4-(3-chlorophenyl)-1,2,4-triazolidin-5-one, 1-fluorodichloromethyl-sulfenyl-3-ethyl-4-(3-chlorophenyl)-1,2,4-triazolidin-5-one, 1-trichloromethyl-sulfenyl-3-propyl-4-(3-chlorophenyl)-1,2,4-triazolidin-5-one, 1-trichloromethyl-sulfenyl-3-isopropyl-4-(3-chlorophenyl)-1,2,4-triazolidin-5-one, 1-fluorodichloromethyl-sulfenyl-3-isopropyl-4-(3-chlorophenyl)-1,2,4-triazolidin-5-one, 1-trichloromethyl-sulfenyl-3-methoxymethyl-4-(3-chlorophenyl)-1,2,4-triazolidin-5-one, 1-trichloromethyl-sulfenyl-3-(2-methoxyethyl)-4-(3-chlorophenyl)-1,2.4-triazolidin-5-one, 1-fluorodichloromethyl-sulfenyl-3-(2-methoxyethyl)-4-(3-chlorophenyl)-1,2,4-triazolidin-5-one, 1-trichloromethylsulfenyl-3-cyclopropyl-4-(3-chlorophenyl)-1,2,4-triazolidin-5-one, 1-fluorodichloromethyl-sulfenyl-3-cyclopropyl-4-(3-chlorophenyl)-1,2,4-triazolidin-5-one, 1-trichloromethyl-sulfenyl-3-cyclohexyl-4-(3-chlorophenyl)-1,2,4-triazolidin-5-one, 1-trichloromethyl-sulfenyl-3-methyl-4-(2-fluorophenyl)-1,2,4-triazolidin-5-one, 1-fluorodichloromethyl-sulfenyl-3-methyl-4-(2-fluorophenyl)-

1,2,4-triazolidin-5-one, 1-trichloromethyl-sulfenyl-3-methyl-4-(2-fluorophenyl)-1,2,4-triazolidin-5-one, 1-trichloromethyl-sulfenyl-3-isopropyl-4-(2-fluorophenyl)-1,2,4-triazolidin-5-one, 1-fluorodichloromethyl-sulfenyl-3-isopropyl-4-(2-fluorophenyl)-1,2,4-triazolidin-5-one, 1-trichloromethyl-sulfenyl-3-cyclopropyl-4-(2-fluorophenyl)-1,2,4-triazolidin-5-one, 1-fluorodichloromethyl-sulfenyl-3-cyclopropyl-4-(2-fluorophenyl)-1,2,4-triazolidin-5-one, 1-trichloromethyl-sulfenyl-3-methyl-4-(4-bromophenyl)-1,2,4-triazolidin-5-one, 1-fluorodichloromethyl-sulfenyl-3-methyl-4-(4-bromophenyl)-1,2,4-triazolidin-5-one, 1-trichloromethyl-sulfenyl-3-isopropyl-4-(4-bromophenyl)-1,2,4-triazolidin-5-one, 1-fluorodichloromethyl-sulfenyl-3-isopropyl-4-(4-bromophenyl)-1,2,4-triazolidin-5-one, 1-trichloromethyl-sulfenyl-3-cyclopropyl-4-(4-bromophenyl)-1,2,4-triazolidin-5-one, 1-fluorodichloromethyl-sulfenyl-3-cyclopropyl-4-(4-bromophenyl)-1,2,4-triazolidin-5-one, 1-fluorodichloromethyl-sulfenyl-3-methyl-4-(3,4-dichlorophenyl)-1,2,4-triazolidin-5-one, 1-trichloromethyl-sulfenyl-3-isopropyl-4-(3,4-dichlorophenyl)-1,2,4-triazolidin-5-one, 1-trichloromethyl-sulfenyl-3-tert.-butyl-4-(3,4-dichlorophenyl)-1,2,4-triazolidin-5-one, 1-trichloromethylsulfenyl-3-methyl-4-(3,5-dichlorophenyl)-1,2,4-triazolidin-5-one, 1-fluorodichloromethyl-sulfenyl-3-methyl-4-(3,5-dichlorophenyl)-1,2,4-triazolidin-5-one, 1-trichloromethylsulfenyl-3-ethyl-4-(3,5-dichlorophenyl)-1,2,4-triazolidin-5-one, 1-fluorodichloromethyl-sulfenyl-3-ethyl-4-(3,5-dichlorophenyl)-1,2,4-triazolidin-5-one, 1-trichloromethylsulfenyl-3-propyl-4-(3,5-dichlorophenyl)-1,2,4-triazolidin-5-one, 1-fluorodichloromethyl-sulfenyl-3-propyl-4-(3,5-dichlorophenyl)-1,2,4-triazolidin-5-one, 1-trichloromethyl-sulfenyl-3-isopropyl-4-(3,5-dichlorophenyl)-1,2,4-triazolidin-5-one, 1-fluorodichloromethyl-sulfenyl-3-isopropyl-4-(3,5-dichlorophenyl)-1,2,4-triazolidin-5-one, 1-trichloromethyl-sulfenyl-3-methoxymethyl-4-(3,5-dichlorophenyl)-1,2,4-triazolidin-5-one, 1-trichloromethyl-sulfenyl-3-isobutyl-4-(3,5-dichlorophenyl)-1,2,4-triazolidin-5-one, 1-trichloromethyl-sulfenyl-3-methyl-4-(3-methoxyphenyl)-1,2,4-triazolidin-5-one, 1-fluorodichloromethyl-sulfenyl-3-methyl-4-(3-methoxyphenyl)-1,2,4-triazolidin-5-one, 1-trichloromethyl-sulfenyl-3-isopropyl-4-(3-methoxyphenyl)-1,2,4-triazolidin-5-one, 1-trichloromethyl-sulfenyl-3-methyl-4-(4-methoxyphenyl)-1,2,4-triazolidin-5-one, 1-fluorodichloromethyl-sulfenyl-3-methyl-4-(4-methoxyphenyl)-1,2,4-triazolidin-5-one, 1-trichloromethyl-sulfenyl-3-ethyl-4-(4-methoxyphenyl)-1,2,4-triazolidin-5-one, 1-fluorodichloromethyl-sulfenyl-3-ethyl-4-(4-methoxyphenyl)-1,2,4-triazolidin-5-one, 1-trichloromethyl-sulfenyl-3-isopropyl-4-(4-methoxyphenyl)-1,2,4-triazolidin-5-one, 1-trichloromethyl-sulfenyl-3-isobutyl-4-(4-methoxyphenyl)-1,2,4-triazolidin-5-one, 1-fluorodichloromethyl-sulfenyl-3-isopropyl-4-(4-methoxyphenyl)-1,2,4-triazolidin-5-one, 1-fluorodichloromethyl-sulfenyl-3-isobutyl-4-(4-methoxyphenyl-1,2,4-triazolidin-5-one, 1-trichloromethyl-sulfenyl-3-cyclopropyl-4-(4-methoxyphenyl)-1,2,4-triazolidin-5-one, 1-trichloromethyl-sulfenyl-3-methyl-4-(4-exthoxyphenyl)-1,2,4-triazolidin-5-one, 1-trichloromethyl-sulfenyl-3-isopropyl-4-(4-ethoxyphenyl)-1,2,4-triazolidin-5-one, 1-fluorodichloromethyl-sulfenyl-3-isopropyl-4-(4-ethoxyphenyl)-1,2,4-triazolidin-5-one, 1-trichloromethyl-sulfenyl-3-methyl-4-(3-chloro-4-methoxyphenyl)-1,2,4-triazolidin-5-one, 1-fluorodichloromethyl-sulfenyl-3-methyl-4-(3-chloro-4-methoxyphenyl)-1,2,4-triazolidin-5-one, 1-trichloromethyl-sulfenyl-3-ethyl-4-(3-chloro-4-methoxyphenyl)-1,2,4-triazolidin-5-one, 1-fluorodichloromethylsulfenyl-3-ethyl-4-(3-chloro-4-methoxyphenyl)-1,2,4-triazolidin-5-one, 1-trichloromethyl-sulfenyl-3-isopropyl-4-(3-chloro-4-methoxyphenyl)-1,2,4-triazolidin-5-one, 1-fluorodichloromethyl-sulfenyl-3-isopropyl-4-(3-chloro-4-methoxyphenyl)-1,2,4-triazolidin-5-one, 1-trichloromethylsulfenyl-3-cyclopropyl-4-(3-chloromethoxyphenyl)-1,2,4-triazolidin-5-one, 1-fluorodichloromethyl-sulfenyl-3-cyclopropyl-4-(3-chloro-4-methoxyphenyl)-1,2,4-triazolidin-5-one, 1-trichloromethyl-sulfenyl-3-isobutyl-4-(3-chloro-4-methoxyphenyl)-1,2,4-triazolidin-5-one, 1-trichloromethyl-sulfenyl-3-cyclohexyl-4-(3-chloro-4-methoxyphenyl)-1,2,4-triazolidin-5-one, 1-trichloromethyl-sulfenyl-3-isopropyl-4-(3-chloro-4-ethoxyphenyl)-1,2,4-triazolidin-5-one, 1-fluorodichloromethyl-sulfenyl-3-isopropyl-4-(3-chloro-4-ethoxyphenyl)-1,2,4-triazolidin-5-one, 1-trichloromethyl-sulfenyl-3-methyl-4-(4-methylphenyl)-1,2,4-triazolidin-5-one, 1-trichloromethyl-sulfenyl-3-isopropyl-4-(4-methylphenyl)-1,2,4-triazolidin-5-one, 1-fluorodichloromethyl-sulfenyl-3-isopropyl-4-(4-methylphenyl)-1,2,4-triazolidin-5-one, 1-trichloromethyl-sulfenyl-3-methyl-4-(3-tert.-butylphenyl)-1,2,4-triazolidin-5-one, 1-trichloromethyl-sulfenyl-3-isopropyl-4-(3-tert.-butylphenyl)-1,2,4-triazolidin-5-one, 1-fluorodichloromethylsulfenyl-3-isopropyl-4-(3-tert.-butylphenyl)-1,2,4-triazolidin-5-one, 1-trichloromethyl-sulfenyl-3-methyl-4-(4-tert.-butylphenyl)-1,2,4-triazolidin-5-one, 1-trichloromethyl-sulfenyl-3-isopropyl-4-(4-tert.-butylphenyl)-1,2,4-triazolidin-5-one, 1-fluorodichloromethyl-sulfenyl-3-isopropyl-4-(4-tert.-butylphenyl)-1,2,4-triazolidin-5-one, 1-trichloromethyl-sulfenyl-3-methyl-4-(4-trifluoromethylphenyl)-1,2,4-triazolidin-5-one, 1-fluorodichloromethyl-sulfenyl-3-methyl-4-(4-trifluoromethylphenyl)-1,2,4-triazolidin-5-one, 1-trichloromethyl-sulfenyl-3-methyl-4-(3-trifluoromethylphenyl)-1,2,4-triazolidin-5-one, 1-fluorodichloromethyl-sulfenyl-3-methyl-4-(3-trifluoromethylphenyl)-1,2,4-triazolidin-5-one, 1-fluorodichloromethyl-sulfenyl-3-isopropyl-4-(3-trifluoromethylphenyl)-1,2,4-triazolidin-5-one, 1-trichloromethyl-sulfenyl-3-cyclopropyl-4-(3-trifluoromethylphenyl)-1,2,4-triazolidin-5-one, 1-fluorodichloromethyl-sulfenyl-3-cyclopropyl-4-(3-trifluoromethylphenyl)-1,2,4-triazolidin-5-one, 1-trichloromethyl-sulfenyl-3-methyl-4-(3,5-dichloro-4-methoxyphenyl)-1,2,4-triazolidin-5-one, 1-fluorodichloromethyl-sulfenyl-3-methyl-4-(3,5-dichloro-4-methoxyphenyl)-1,2,4-triazolidin-5-one, 1-trichloromethyl-sulfenyl-3-methyl-4-(4-nitrophenyl)-1,2,4-triazolidin-5-one, 1-trichloromethyl-sulfenyl-3-isopropyl-4-(4-nitrophenyl)-1,2-triazolidin-5-one and 1-trichloromethyl-sulfenyl-3-methyl-4-(4-biphenylyl)-1,2,4-triazolidin-5-one.

EXAMPLE 1

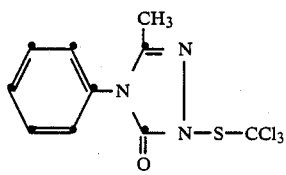

19 g (0.102 mole) of perchloromethylmercaptan and 10 g (0.099 mole) of triethylamine were added dropwise, in succession, to a suspension of 17.5 g (0.1 mole) of 3-methyl-4-phenyl-1,2,4-triazolidin-5-one in 150 ml of dry ethyl acetate at from about 10° to 15° C., with thorough stirring. After the mixture had been stirred for two hours at room temperature (20° C.), the triethylamine hydrochloride precipitated was filtered off with suction and washed with 40 ml of ethyl acetate. The filtrate was extracted twice by shaking with 100 ml portions of water, dried over $Na_2SO_4$ and concentrated by evaporation of the solvent. After addition of 20 ml of ether, the residue crystallized at 0° C. 30.15 g (84% of theory) of 1-trichloromethyl-sulfenyl-3-methyl-4-phenyl-1,2,4-triazolidin-5-one were obtained as white crystals of melting point 142°–144° C. (No. 1).

EXAMPLE 2

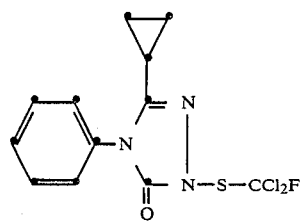

20.1 g (0.1 mole) of 3-cyclopropyl-4-phenyl-1,2,4-triazolidin-5-one were reacted with 17 g (0.1 mole) of fluorodichloromethyl-sulfenyl chloride by a procedure similar to that described in Example 1. 21.4 g (71% of theory) of 1-fluorodichloromethyl-sulfenyl-3-cyclopropyl-4-phenyl-1,2,4-triazolidin-5-one were obtained as white crystals of melting point 81°–83° C. (No. 2).

The following compounds of the formula I were prepared in a similar manner and were characterized by infra-red and nuclear magnetic resonance spectroscopy and by elemental analysis.

| Ex. no. | X | R | Y | Infrared spectrum [KBr][cm$^{-1}$] or melting point °C. |
|---|---|---|---|---|
| 3 | H | —$CH_2$—O—$CH_3$ | Cl | 85–87 |
| 4 | H | —$C_2H_5$ | Cl | 100–102 |
| 5 | H | —$C_3H_7$—n | Cl | resin |
| 6 | H | —$C_3H_7$—i | Cl | 116–118 |
| 7 | H | —cyclopropyl | Cl | 122–123 |
| 8 | H | —$CH_2$—$CH_2$—O—$CH_3$ | Cl | 3060, 1730, 1580, 1400, 1200, 1003, 800, 750, |
| 9 | H | —$CH_2$—$CH_2O$—$CH_3$ | F | 3065, 1730, 1578, 1400, 1210, 1040, 810, 759 |
| 10 | H | —$CH(CH_3)CH_2CH_2CH_3$ | Cl | 80–84 |
| 11 | H | —$CH(CH_3)CH_2CH_2$—$CH_3$ | F | 72–75 |
| 12 | H | —cyclohexyl | Cl | 117–120 |
| 13 | 4-F | —$CH_3$ | Cl | 145–147 |
| 15 | 4-F | —$C_3H_7$—i | Cl | 105–107 |
| 16 | 2-F | —cyclopropyl | Cl | 136 |
| 17 | 2-F | —cyclopropyl | F | 109–110 |
| 18 | 3-Cl | —$CH_3$ | Cl | 120–122 |
| 19 | 3-Cl | —$C_2H_5$ | Cl | 105–107 |
| 20 | 3-Cl | —$C_3H_7n$ | Cl | 62–64 |
| 21 | 3-Cl | —$C_3H_7$—i | Cl | 140–142 |
| 22 | 3-Cl | —$CH_2CH_2$—O—$CH_3$ | Cl | 3065, 1730, 1580, 1395, 1205, 1105, 800, 780, 745 |
| 23 | 3-Cl | —$CH_2CH_2$—O—$CH_3$ | F | 3065, 1730, 1470, 1210, 1105, 1040, 810, 780, 680 |
| 24 | 3-Cl | cyclopropyl | Cl | 3070, 1730, 1580, 1420, 1210, |
|    |      |             | Cl | 3070, 1730, 1580, 1420, 1210, 1060, 780, 490 |
| 25 | 3-Cl | cyclopropyl | F | 3070, 1730, 1474, 1418, 1210, 1080, 810, 780, 742 |
| 28 | 4-Br | —$CH_3$ | Cl | 3080, 1735, 1482, 1210, 1112, 100, 802, 750 |
| 29 | 4-Br | —$CH_3$ | F | 3080, 1735, 1482, 1210, 1112, 1000, 802, 750 |
| 30 | 4-Br | —cyclopropyl | Cl | 3090, 1735, 1582, 1;20, 1210, 990, 810, 750 |
| 31 | 4-Br | —Cyclopropyl | F | 3090, 1730, 1530, 1210, 1065, 989, 808, 740 |
| 32 | 3,5-$Cl_2$ | —$C_3H_7$—n | Cl | 71–73 |
| 33 | 4-$CH_3$ | —$C_3H_7$—i | Cl | 114–116 |
| 34 | 3-$C(CH_3)_3$ | —$CH_3$ | Cl | 141–143 |
| 35 | 3-$CF_3$ | —$CH_3$ | Cl | 3085, 1735, 1587, 1323, 1210, 1065, 803, 752 |
| 36 | 3-$CF_3$ | —$CH_3$ | F | 3080, 1730, 1585, 1325, 1170, 1042, 840, 810 |
| 37 | 3-$CF_3$ | —cyclopropyl | Cl | 92 |
| 38 | 3-$CF_3$ | —cyclopropyl | F | 55–57 |
| 39 | 3-$CH_3O$— | —$CH_3$ | Cl | 101–102 |
| 40 | 3-$CH_3O$— | —$CH_3$ | F | 3059, 2925, 1730, 1585, 1480, 1390, 1230, 1032, 830, 810, 728, 678 |

-continued

| Ex. no. | X | R | Y | Infrared spectrum [KBr][cm$^{-1}$] or melting point °C. |
|---|---|---|---|---|
| 41 | 4-CH$_3$O— | —CH$_3$ | Cl | 136–138 |
| 42 | 4-CH$_3$O— | —C$_2$H$_5$ | Cl | 128–130 |
| 43 | 4-CH$_3$O— | —C$_3$H$_7$—i | Cl | 99–101 |
| 44 | 4-CH$_3$O— | —C$_3$H$_7$—i | F | 81–82 |
| 45 | 3-Cl, 4-CH$_3$O— | —CH$_3$ | Cl | 156–158 |
| 46 | 4-F | —C$_3$H$_7$—i | F | 78–80 |
| 47 | 3-Cl, 4-CH$_3$O | —C$_3$H$_7$—i | F | 120–121 |
| 48 | 3-Cl, 4-CH$_3$O | —C$_3$H$_7$—i | Cl | 148–150 |
| 49 | 3-Cl, 4-CH$_3$O | —C$_2$H$_5$ | F | 102–103 |
| 50 | 3-Cl, 4-CH$_3$O | —cyclohexyl | F | 68–70 |
| 51 | 3-Cl, 4-CH$_3$O | —cyclohexyl | Cl | 124–126 |
| 52 | 3-Cl, 4-CH$_3$O | —CH$_3$ | F | 96–97 |
| 53 | 3-Cl, 4-CH$_3$O | —C$_2$H$_5$ | Cl | 108–110 |
| 54 | 3-Cl, 4-CH$_3$O | —CH$_2$—O—CH$_3$ | F | 98–100 |
| 55 | 3-Cl, 4-CH$_3$O | —CH$_2$—O—CH$_3$ | Cl | 130–132 |
| The following compounds may be prepared analogously: | | | | |
| 14 | 4-F | —CH$_3$ | F | |
| 26 | 4-Cl | —CH$_3$ | Cl | |
| 27 | 4-Cl | —CH$_3$ | F | |

The novel compounds have an excellent action on a broad spectrum of plant-pathogenic fungi. They may be used as soil and foliar fungicides.

The novel compounds are especially suitable for combating the following plant diseases:

*Phytophthora infestans* in tomatoes and potatoes,
*Phytophthora parasitica* in strawberries,
*Phytophthora cactorum* in apples,
*Pseudoperonospora cubensis* in cucumbers,
*Pseudoperonospora humuli* in hops,
*Peronospora destructor* in onions,
*Peronospora sparsa* in roses,
*Peronospora tabacina* in tobacco,
*Plasmopara viticola* in grapes,
*Plasmopara halstedii* in sunflowers,
*Pythium ultimum* in pea seedlings,
*Botrytis cinerea* in grapes, strawberries and pimientos,
*Septoria nodorum* in cereals, and
*Venturia inaequalis* in apple trees.

The compounds are applied by spraying or dusting the plants with the active ingredients or treating the seeds of the plants with the active ingredients. They may be applied before or after infection of the plants or seeds by the fungi.

The novel compounds can be converted into the conventional formulations, e.g. solutions, emulsions, suspensions, dusts, powders, pastes and granules. The form in which the compound is applied depends entirely on the end use but should in every case ensure a fine and uniform distribution of the active ingredient. The formulations are prepared in conventional manner, for example by diluting the active ingredient with solvents and/or carriers, with or without the addition of emulsifiers and dispersants, and, where water is used as the diluent, with or without an organic auxiliary solvent. Suitable auxiliaries are, essentially, solvents, for example aromatics, e.g., xylene and benzene, chloroaromatics, e.g., chlorobenzenes, paraffins, e.g., petroleum fractions, alcohols e.g., methanol, and butanol, amines, e.g., ethanolamine and dimethylformamide, and water; carriers, for example natural rock powders, e.g., kaolin, alumina, talc and chalk, and synthetic rock powders, e.g., highly disperse silica and silicates; emulsifiers, for example non-ionic and anionic emulsifiers, e.g., polyoxyethylene fatty alcohol ethers, alkylsulfonates and arylsulfonates, and dispersants, for example lignin, sulfite waste liquors and methylcellulose.

The fungicidal agents in general contain from 0.1 to 95% by weight of active ingredient, preferably from 0.5 to 90%.

The amounts used depend on the nature of the desired effect, and range from 0.1 to 3 kg and more of active ingredient per hectare. The new compounds may also be used for the protection of materials. When they are used for example as fungicides for paints and soft PVC, the application rates are from 0.05 to 5% (wt%) of active ingredient, based on the total weight of the paint to be preserved or the PVC to be microbicidally finished. The new active ingredients may further be used as fungicidally active components of oily wood preservatives for the protection of wood against wood-discoloring fungi. The wood is treated with these agents for instance by impregnation or coating.

The agents, and the ready-to-use formulations obtained therefrom, e.g., solutions, emulsions, suspensions, powders, dusts, pastes or granules, are applied in the conventional manner, e.g. by spraying, atomizing, dusting, scattering, treating seed or watering.

Examples of such formulations are given below.

I. 90 parts by weight of the compound of Example 1 is mixed with 10 parts by weight of N-methyl-alpha-pyrrolidone. A mixture is obtained which is suitable for application in the form of very fine drops.

II. 10 parts by weight of the compound of Example 3 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of the compound of Example 4 is dissolved in a mixture consisting of 60 parts by weight of cyclohexanone, 30 parts by weight of isobutanol, and 10 parts by weight of the adduct of 40 moles of ethylene oxide and 1 mole of castor oil. By pouring the solution into water and finely distributing it therein, an aqueous dispersion is obtained.

IV. 20 parts by weight of the compound of Example 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of the compound of Example 10 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of the compound of Example 11 is intimately mixed with 97 parts by weight of particulate kaolin. A dust is obtained containing 3% by weight of the active ingredient.

VII. 30 parts by weight of the compound of Example 12 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 13 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of the compound of Example 17 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may, in these application forms, contain other active ingredients together with those according to the invention, e.g., herbicides, insecticides, growth regulators and other fungicides, or may be mixed with fertilizers and applied together with these. When the active ingredient are mixed with other fungicides, the fungicidal spectrum of action is in many cases broadened.

The list of fungicides given below, with which the compounds according to the invention can be combined, is intended to illustrate the possible combinations, but the invention is in no way limited to these.

Examples of fungicides which can be combined with the compounds of the invention are: sulfur, dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-dissulfide, nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-(1,1,2,2-tetrachloroethylthio)-tetrahydrophthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 4-(2-chlorophenylhydrazone)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, alpha-(2-chlorophenyl)-alpha-(4-chlorophenyl)-5-pyrimidinemethanol, organo-tin compounds, such as tributyl tin oxide and tributyl tin benzoate, methylene bis-thiocyanate, alkyl-dimethylbenzylammonium chloride, cetylpyridinium chloride, chlorinated phenols, such as tetrachlorophenol and pentachlorophenol, tetrachloroisophthalic acid dinitrile, N-cyclohexyl-N-methoxy-2,5-dimethylfuran-3-carboxylic acid amide, 2,4,5-trimethyl-furan-carbooxylic acid anilide, N-phenyl-N,N'-dimethyl-N'-fluorodichloromethyl-thiosulfonyldiamide, 2-thiocyanomethyl-thiobenzothiazole, mercaptobenzothiazole, copper naphthenate, alkali metal and metal salts of N'-hydroxy-N-cyclohexyl-diazenium oxide, p-chlorophenyl-3-propargyl-formate, and 3-iodo-2-propynyl-butyl carbamate.

For the experiments described below, the following active ingredients were employed for comparison purposes:

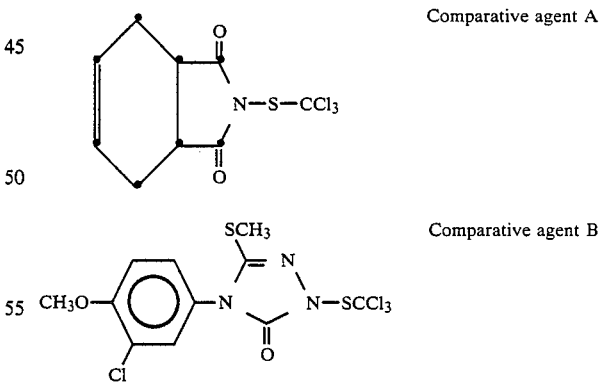

Comparative agent A

Comparative agent B

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity to obtain optimum conditions for promoting fungus growth. After 5 days, the disease had spread to such a great extent on the untreated plants that the necroses covered the major portion of the leaves.

The results revealed that for example compounds 1, 3, 4, 6, 10, 11, 12, 13, 17, 28, 29, 35, 36 and 45, applied as 0.05% sprays, had a better fungicidal action (e.g., 100%) than prior art compound A (e.g., 70%).

EXPERIMENT 2

Action on *Phytophthora infestans* in tomatoes

Leaves of potted tomatoes of the "Grosse Fleischtomate" variety were sprayed with aqueous suspensions containing (dry basis) 80% of active ingredient and 20% of emulsifier. After the sprayed-on layer had dried, the leaves were infected with a zoospore suspension of *Phytophthora infestans*. The plants were then placed for 5 days in a water vapor-saturated chamber kept at 16° to 18° C. After this period, the disease had spread on the untreated control plants to such an extent that the fungicidal action of the compounds was able to be assessed.

The results of the experiment revealed that for example compounds 1, 6, 13, 17, 18, 24, 28, 39 and 45, applied as 0.025% sprays, had a better fungicidal action (e.g., 97%) than compound A (e.g., 60%).

EXPERIMENT 3

Action on *Septoria nodorum*

The leaves of pot-grown wheat seedlings of the "Jubilar" variety were sprayed with aqueous liquors containing (dry basis) 80% of active ingredient and 20% of emulsifier. After the sprayed-on layer had dried, the leaves were cut off and placed in dishes containing aqueous benzimidazole solution (25 ppm). The leaves were then infected with an aqueous suspension of spores of *Septoria nodorum*, and covers were placed on the dishes. After 7 days at 20° to 22° C., the extent of fungus spread was assessed.

The results show that for example active ingredients 3, 7, 12, 28, 30, 35 and 39, applied as 0.1% sprays, had a good fungicidal action (e.g., 100%).

EXPERIMENT 4

Action on wood-discoloring fungi

To prepare an oily wood preservative containing 1% (wt%) of active ingredient, 1 part (by weight) of the compound of Example 2 was dissolved, with slight heating, in 55 parts of a gasoline fraction rich in aromatics. 10 parts of an alkyd resin was then added, and the composition was then made up to 100 parts at room temperature by adding gasoline. Oily wood preservatives containing 0.25 to 5 wt% of the active ingredients of Examples 2 and 40 were prepared in the same way.

A groove was made with a saw in the middle of pine sapwood boards measuring 93×45×9 mm, giving two equally large square surfaces. One surface served as control and the other was treated twice, each time with 100 g/m², of the wood preservatives. The control surfaces were treated with the same amounts of linseed oil varnish containing no active ingredient. After 1 to 2 days, the top side of each board was coated with an oil-modified alkyd-based resin finish. Three days after this finish had been applied the boards were placed in a shade-free position in the open on wooden grilles and weathered in this horizontal position for 6 months. Subsequently the boards were placed in 500 cm³ glass flasks and after the boards had been sterilized with propylene oxide they were artificially infected with the fungi *Pullularia pullulans* and *Sclerophoma pityophila* which had been cultivated in a 2% malt extract solution. The temperature at which the flasks were then kept for 6 weeks was 20° to 23° C., and the humidity at least 75%.

On conclusion of the experiment, 90% of the untreated control surfaces was blue as a result of the action of the fungi *Pullularia pullulans* and *Schlerophoma pityophila;* the wood was also blue underneath the surface. The surfaces treated with wood preservatives containing 1% of the active ingredients of Examples 2 and 40 showed no signs of discoloration. The insides of the wood blocks also showed no blue discoloration.

EXPERIMENT 5

Action on *Phytophthora infestans* in tomatoes

Leaves of potted tomatoes of the "Grosse Fleischtomate" variety were sprayed with aqueous suspensions containing (dry basis) 80% of active ingredient and 20% of emulsifier. After the sprayed-on layer had dried, the leaves were infected with a zoospore suspension of *Phytophthora infestans*. The plants were then placed for 5 days in a water vapor-saturated chamber kept at 16° to 18° C. After this period, the disease had spread on the untreated control plants to such an extent that the fungicidal action of the compounds was able to be assessed.

The results show that for example compound 45, applied as a 0.05, 0.025 and 0.012% spray, had a better fungicidal action (e.g., 100%) than the active ingredient B (e.g., 70).

We claim:

1. A 1-(trihalomethylsulfenyl)-4-aryl-1,2,4-triazolin-5-one of the formula

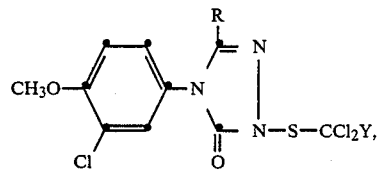

where R is alkyl of 1 to 6 carbon atoms which is unsubstituted or substituted by methoxy or ethoxy, or is alkenyl of 2 to 6 carbon atoms, or is cycloalkyl of 3 to 7 carbon atoms which is unsubstituted or substituted by methoxy, and Y is chlorine.

2. A 1-(trihalomethyl-sulfenyl)-4-aryl-1,2,4-triazolidin-5-one as defined in claim 1, wherein R is methyl.

3. A process for combating fungi, wherein the fungi or the objects to be protected against fungus attack are treated with an effective amount of a 1-trihalomethylsulfenyl)-4-aryl-1,2,4-triazolin-5-one of the formula

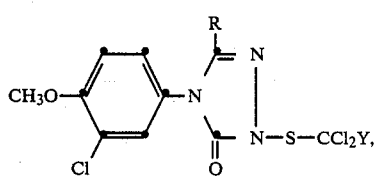

where R is alkyl of 1 to 6 carbon atoms which is unsubstituted or substituted by methoxy or ethoxy, or is alkenyl of 2 to 6 carbon atoms, or is cycloalkyl of 3 to 7 carbon atoms which is unsubstituted or substituted by methoxy, and Y is chlorine.

* * * * *

UNITED STATES PATENT AND TRADEMARK OFFICE
CERTIFICATE OF CORRECTION

PATENT NO. : 4,804,671
DATED : Feb. 14, 1989
INVENTOR(S) : RENTZEA et al.

It is certified that error appears in the above-identified patent and that said Letters Patent is hereby corrected as shown below:

Title page:

INVENTORS:

The First Inventor's name is incorrectly listed as:
"Rentzea, Costin;Heidelberg"

The Inventor's correct name is:

"Costin, Rentzea, Heidelberg;"

Item [19] "Costin et al." should read --Rentzea et al.--.

Signed and Sealed this

Sixth Day of February, 1990

*Attest:*

JEFFREY M. SAMUELS

*Attesting Officer*   *Acting Commissioner of Patents and Trademarks*